US007728183B2

(12) United States Patent
Nappa et al.

(10) Patent No.: US 7,728,183 B2
(45) Date of Patent: Jun. 1, 2010

(54) SELECTIVELY REACTING OLEFINS HAVING A TERMINAL CF2 GROUP IN A MIXTURE

(75) Inventors: Mario Joseph Nappa, Newark, DE (US); Allen Capron Sievert, Elkton, MD (US); Victor Filippovich Cherstkov, Moscow (RU); Nina Ivanova Delyagina, Moscow (RU)

(73) Assignee: E.I. du Pont de Nemours and Company, Wilmington, DE (US)

( * ) Notice: Subject to any disclaimer, the term of this patent is extended or adjusted under 35 U.S.C. 154(b) by 25 days.

(21) Appl. No.: 12/278,789

(22) PCT Filed: Apr. 3, 2007

(86) PCT No.: PCT/US2007/008050

§ 371 (c)(1),
(2), (4) Date: Aug. 8, 2008

(87) PCT Pub. No.: WO2007/123786

PCT Pub. Date: Nov. 1, 2007

(65) Prior Publication Data

US 2009/0012336 A1 Jan. 8, 2009

(51) Int. Cl.
*C07C 17/38* (2006.01)
(52) U.S. Cl. .................................. 570/177; 570/238
(58) Field of Classification Search ................. 570/177, 570/238
See application file for complete search history.

(56) References Cited

U.S. PATENT DOCUMENTS

| 3,976,759 | A | | 8/1976 | Bennett et al. |
| 4,206,138 | A | | 6/1980 | England |
| 4,235,804 | A | | 11/1980 | Krespan |
| 5,557,020 | A | * | 9/1996 | Von Werner ................. 570/177 |
| 6,143,938 | A | | 11/2000 | Sievert et al. |
| 6,147,267 | A | | 11/2000 | Sievert et al. |
| 2004/0119047 | A1 | | 6/2004 | Singh et al. |

FOREIGN PATENT DOCUMENTS

| EP | 602482 | 6/1994 |
| JP | S45-33046 | 10/1970 |
| SU | 1766912 A1 | 10/1992 |

OTHER PUBLICATIONS

N. P. Aktaev et al., Fluorine-Containing B-Sultones Communication 45. 2-Hydropentafluoropropane-2-B-Sultone, Institute of Heteroorganic Compounds, 1975, pp. 2416-2421.
M. A. Dmitriev et al., Fluorine-Containing B-Sultones Report 1. Addition of Sulfur Trioxide to Fluoroolefins, Proceedings of the Ussr Academy of Sciences, 1960, pp. 1-6.
J. Mohtasham et al., B-Fluorosultones: Synthesis, Reactivity, Structure and Uses, Coordination Chemistry Reviews, 1992, vol. 112:47-79.
R.N. Haszeldine et al., Polyfluorocarbanion Chemistry, Part IV. Some Reactions of 2H- and 1H-Pentafluoropane With Nucleophiles, pp. 2015-2019, 1974.
C.G. Krespan et al., Journal of Fluorine Chemistry, Fluoroolefin Condensation Catalyzed by Aluminum Chlorofluoride, vol. 77, pp. 117-126, 1996.
V.A. Petrov, Journal of Fluorine Chemistry, Reaction of Fluoroolefins With Sulfur Chlorides in Hydrogen Fluoride-Boron Trifluoride Systems, vol. 112, pp. 325-327, 2001.
V.A. Petrov et al., J. Org. Chem., Conjugate Electrophilic Iodofluorination of Fluoroolefins, vol. 61, pp. 9605-9607, 1996.
English-language abstract for SU 1766912 A1, Nov. 30, 1993.

* cited by examiner

*Primary Examiner*—Jafar Parsa

(57) ABSTRACT

A process is disclosed for reducing the mole ratio of (1) compounds of the formula $Y^1Y^2C\!=\!CF_2$ wherein $Y^1$ and $Y^2$ are each independently H, F, Cl, Br, $C_1$-$C_6$ alkyl or $C_1$-$C_6$ haloalkyl containing no more than 3 chlorine substituents, 2 bromine substituents and 1 iodo substituent to (2) saturated compounds of the formula $C_dH_eF_fCl_gBr_hI_k$ wherein d is an integer from 1 to 10, and e+f+g+h+k is equal to 2d+2, provided that g is 0, 1, 2 or 3, h is 0, 1 or 2 and k is 0 or 1 and/or unsaturated compounds of the formula $Y^3Y^4C\!=\!CY^5Y^6$, wherein $Y^3$, $Y^5$ and $Y^6$ are each independently H, F, Cl, Br, $C_1$-$C_6$ alkyl or $C_1$-$C_6$ haloalkyl containing no more than 3 chlorine substituents, 2 bromine substituents and 1 iodo substituent, provided that $Y^5$ and $Y^6$ are not both F, and $Y^4$ is $C_1$-$C_6$ alkyl or $C_1$-$C_6$ haloalkyl containing no more than 3 chlorine substituents, 2 bromine substituents and 1 iodo substituent, in a mixture. The process involves contacting the mixture with at least one selective removal agent selected from the group consisting of $SO_3$ and $RSO_3H$, wherein R is selected from the group consisting of F, Cl, OH, $C_1$-$C_8$ alkyl, $C_1$-$C_8$ fluoroalkyl, and $C_1$-$C_8$ fluoroalkoxyalkyl containing no more than two ether oxygens to selectively react the formula $Y^1Y^2C\!=\!CF_2$ compounds.

10 Claims, No Drawings

SELECTIVELY REACTING OLEFINS HAVING A TERMINAL CF2 GROUP IN A MIXTURE

BACKGROUND OF THE INVENTION

1. Field of the Invention

The present invention relates to processes for reducing the relative content of olefins having a terminal $CF_2$ group in a mixture thereof with hydrocarbons and/or halohydrocarbons by using selective removal agents.

2. Description of Related Art

Halogenated compounds, especially fluorinated compounds, such as fluorocarbons and hydrofluorocarbons, have been widely used as refrigerants, solvents, cleaning agents, foam blowing agents, aerosol propellants, heat transfer media, dielectrics, fire extinguishing agents, sterilants and power cycle working fluids, et al. Purification is an important step in manufacturing these compounds. Distillation is typically used to separate desired products from impurities; however, purification becomes difficult or impossible when the desired compound has a boiling point close to that of one or more of the impurities.

For example, 1,2,3,3,3-pentafluoropropene (HFC-1225ye), having zero ozone depletion and low global warming potentials, has been identified as a potential refrigerant. However, the manufacture of 1,2,3,3,3-pentafluoropropene can also result in the formation of an isomeric contaminant, 1,1,3,3,3-pentafluoropropene (HFC-1225zc). As Singh et al. indicate in US Patent Application 2004/0119047, 1,1,3,3,3-pentafluoropropene exhibits toxicity. However, the boiling point of 1,2,3,3,3-pentafluoropropene is −19.9° C. and the boiling point of 1,1,3,3,3-pentafluoropropene is −21.8° C. Thus, removing 1,1,3,3,3-pentafluoropropene from a mixture containing 1,2,3,3,3-pentafluoropropene and 1,1,3,3,3-pentafluoropropene by distillation is difficult.

There is a need to develop other processes for reducing the relative content of compounds such as 1,1,3,3,3-pentafluoropropene which have a terminal $CF_2$ group.

BRIEF SUMMARY OF THE INVENTION

This invention provides a process for reducing the mole ratio of a (1) first component selected from the group consisting of compounds of the formula $Y^1Y^2C=CF_2$ wherein $Y^1$ and $Y^2$ are each independently H, F, Cl, Br, $C_1$-$C_6$ alkyl or $C_1$-$C_6$ haloalkyl containing no more than 3 chlorine substituents, 2 bromine substituents and 1 iodo substituent to a (2) second component selected from the group consisting of saturated compounds of the formula $C_dH_eF_fCl_gBr_hI_k$ wherein d is an integer from 1 to 10, and e+f+g+h+k is equal to 2d+2, provided that g is 0, 1, 2 or 3, h is 0, 1 or 2 and k is 0 or 1 and unsaturated compounds of the formula $Y^3Y^4C=CY^5Y^6$, wherein $Y^3$, $Y^5$ and $Y^6$ are each independently H, F, Cl, Br, $C_1$-$C_6$ alkyl or $C_1$-$C_6$ haloalkyl containing no more than 3 chlorine substituents, 2 bromine substituents and 1 iodo substituent, provided that $Y^5$ and $Y^6$ are not both F, and $Y^4$ is $C_1$-$C_6$ alkyl or $C_1$-$C_6$ haloalkyl containing no more than 3 chlorine substituents, 2 bromine substituents and 1 iodo substituent, in a mixture comprising said first component and second component. The process comprises contacting said mixture with at least one selective removal agent selected from the group consisting of $SO_3$ and $RSO_3H$, wherein R is selected from the group consisting of F, Cl, OH, $C_1$-$C_8$ alkyl, $C_1$-$C_8$ fluoroalkyl, and $C_1$-$C_8$ fluoroalkoxyalkyl containing no more than two ether oxygens to selectively react said selective removal agent with said first component.

DETAILED DESCRIPTION OF THE INVENTION

This invention involves selective addition reactions which form addition compounds between a compound of the formula $Y^1Y^2C=CF_2$ and a selective removal agent selected from the group consisting of $SO_3$ and $RSO_3H$.

In this invention, the term "alkyl", used either alone or in compound words such as "haloalkyl" includes straight-chain or branched alkyl, such as, methyl, ethyl, n-propyl, i-propyl, or the different isomers thereof. "Alkoxyalkyl" denotes alkoxy substitution on alkyl. Examples of "alkoxyalkyl" include $CH_3OCH_2$, $CH_3CH_2OCH_2$, $CH_3CH_2CH_2CH_2OCH_2$, $CH_3CH_2(CH_3)OCH_2$ and $CH_3CH_2OCH_2CH_2$.

In this invention, the term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $CF_3$, $CH_2Cl$, $CF_3CH_2$ and $CF_3CCl_2$. Consistently, the term "fluoroalkyl" designates haloalkyls partially or fully substituted with only fluorine atoms. Examples of "fluoroalkyl" include $CF_3$, $CF_3CF_2$, $CHF_2CF_2$, and $CF_3CH_2$. The term "fluoroalkoxyalkyl" designates alkoxyalkyls partially or fully substituted with fluorine atoms. Examples of fluoroalkoxyalkyl include $CF_3OCF_2$, $CF_3CF_2OCH_2$, $CF_3CF_2CF_2CF_2OCF_2$, $CF_3OCHFCF_2$, $CH_3CF(CF_3)OCH_2$ and $CF_3CF_2OCF_2CH_2$.

In this invention, the total number of carbon atoms in a substituent group is indicated by the "$C_i$-$C_j$" prefix where i and j denotes the range of the number of carbon atoms. For example, $C_1$-$C_6$ alkyl designates methyl through hexyl; $C_2$ fluoroalkoxyalkyl designates for example $CF_3OCH_2$; $C_3$ fluoroalkoxyalkyl designates, for example, $CF_3OCHFCF_2$; and $C_4$ fluoroalkoxyalkyl designates the various isomers of a fluoroalkyl group substituted with an alkoxy or fluoroalkoxy group containing a total of four carbon atoms, examples including $CF_3CF_2OCHFCF_2$ and $CF_3CF_2OCH_2CH_2$.

Component (1) consists of one or more compounds of the formula $Y^1Y^2C=CF_2$. Examples of these compounds include 1,1,3,3,3-pentafluoropropene (HFC-1225zc), trifluoroethylene (HFC-1123), tetrafluoroethylene (TFE), chlorotrifluoroethylene (CTFE), 1-chloro-2,2-difluoroethene, 2-chloro-1,1,3,3,3-pentafluoro-1-propene (CFC-1215xc), 2-bromo-1,1,3,3,3-pentafluoro-1-propene (CFC-1215xcB), hexafluoropropene (HFP), and perfluoroisobutylene (PFIB), 1,1,2,3,3-pentafluoro-1-propene, 1,1,2,3-tetrafluoro-1-propene, 1,1,3,3-tetrafluoro-1-propene, 1,1,2-trifluoro-1-propene, 1,1,3-trifluoro-1-propene, 1,1,2,3,3,4,4,4-octafluoro-1-butene, 1,1,3,3,4,4,4-heptafluoro-1-butene, 1,1,2,3,4,4,4-heptafluoro-1-butene, 1,1,2,3,3,4,4-heptafluoro-1-butene, 1,1,2,3,3,4-hexafluoro-1-butene, 1,1,2,3,4,4-hexafluoro-1-butene, 1,1,2,3,3-pentafluoro-1-butene, 1,1,3,3,3-pentafluoro-2-methyl-1-propene, 1,1,3,3-tetrafluoro-2-methyl-1-propene, 1,1,2,3,3,4,4,5,5,5-decafluoro-1-pentene, 1,1,3,3,4,4,5,5,5-nonafluoro-1-pentene, 1,1,2,3,3,4,4,5,5-nonafluoro-1-pentene, 1,1,2,4,4,4-hexafluoro-3-(trifluoromethyl)-1-butene, 1,1,3,4,4,4-hexafluoro-3-(trifluoromethyl)-1-butene, 1,1,4,4,4-pentafluoro-3-(trifluoromethyl)-1-butene, 1,1,4,4,4-pentafluoro-2-(trifluoromethyl)-1-butene, 1,1,3,3,5,5,5-heptafluoro-1-pentene, 1,1,2,3,3,4,4,5,5,6,6,6-dodecafluoro-1-hexene. Of particular note are component (1) compounds selected from the group consisting of 1,1,3,3,3-pentafluoropropene (HFC-1225zc), trifluoroethylene (HFC-1123), tetrafluoroethylene (TFE), chlorotrifluoroethylene (CTFE), 1-chloro-2,2-difluoroethene, 2-chloro-1,1,3,3,3-pentafluoro-1-propene (CFC- 1215xc), 2-bromo-1,1,3,3,3-pentafluoro-1-propene (CFC-1215xcB), hexafluoropropene (HFP), and perfluoroisobutylene (PFIB), 1,1,2,3,3-pentafluoro-1-propene, 1,1,2,3-tetrafluoro-1-propene, 1,1,3,3-tetrafluoro-1-propene, 1,1,2-trifluoro-1-propene, 1,1,3-trifluoro-1-propene.

Representative selective removal agents in this invention include, but are not limited to, $SO_3$, oleum, fluorosulfonic acid, chlorosulfonic acid, difluoromethanesulfonic acid, trifluoromethanesulfonic acid, pentafluoroethanesulfonic acid 1,1,2,2-tetrafluoroethanesulfonic acid, 1,1,1,2-tetrafluoroethanesulfonic acid, 1,1,1,2,3,3-hexafluoropropanesulfonic acid, 1,1,1,2-tetrafluoro-2-(trifluoromethyl)ethanesulfonic acid, 1,1,2-trifluoro-2-(trifluoromethoxy)ethanesulfonic acid, and methane sulfonic acid.

In this invention, the term "addition compound" means the compounds formed in the addition reactions between selective removal agents and the component (1) compound(s) of the formula $Y^1Y^2C=CF_2$. The addition reactions between selective removal agents and compounds of the formula $Y^1Y^2C=CF_2$ typically result in addition compounds which have higher boiling points than the starting olefin compounds. In one embodiment of this invention, the addition compounds formed in the addition reactions between selective removal agents and compounds of the formula $Y^1Y^2C=CF_2$ are fluorine-containing β-sultones. For example, as demonstrated in Example 3 below, $SO_3$ and 1,1,3,3,3-pentafluoropropene can react at room temperature to form 1,1,3,3,3-pentafluoropropane-β-sultone.

In another embodiment of this invention, the addition compounds formed in the addition reactions between selective removal agents and compounds of the formula $Y^1Y^2C=CF_2$ are sulfate addition products. For example, as demonstrated in Example 1 below, fluorosulfonic acid and 1,1,3,3,3-pentafluoropropene can react at room temperature to form sulfate $CF_3CH_2CF_2OSO_2F$.

The representative compounds and embodiment descriptions exemplified in the specification are illustrative of the invention, and shall not be construed as limiting to the scope of this invention.

The addition compounds formed in the addition reactions between selective removal agents and compounds of the formula $Y^1Y^2C=CF_2$ can be further transformed into other chemical compounds. For example, fluorine-containing β-sultones can be hydrolyzed to form sulfonyl fluorides and sulfonic acids. Fluorine-containing β-sultones can also react with alcohols to form esters. Reactions of fluorine-containing β-sultones have been described by Aktaev et al., in Izvestiya Akademii Nauk SSSR, Seriya Khimicheskaya, No. 11, pp. 2530-2535, November, 1975, and by Mohtasham, et al., in Coordination Chemistry Reviews, 112, 47-79, (1992), herein incorporated as reference.

The mixture treated in accordance with this invention comprises (1) at least one compound of the formula $Y^1Y^2C=CF_2$ and (2) at least one compound of the formula $C_dH_eF_fCl_gBr_hI_k$ and/or at least one compound of the formula $Y^3Y^4C=CY^5Y^6$. Of note are mixtures of compounds where $Y^1$ is selected from H, F, and $C_1$-$C_3$ perfluoroalkyl and $Y^2$ is selected from H and F; d is 2 to 5; and g, h, and k are 0 and $Y^3$ and $Y^5$ are each independently H or F, and $Y^4$ is $C_1$ to $C_3$ perfluoroalkyl, and $Y^6$ is H, F, or $C_1$ to $C_3$ perfluoroalkyl (provided that $Y^5$ and $Y^6$ are not both F) The mixtures may also contain other components. For example, when the mixture results from a component (2) production process, HF and HCl may be present. Other residual contaminants may include air, nitrogen, and/or solvents from production processes.

The selective addition reactions are used to reduce the mole ratio of the compound(s) of the formula $Y^1Y^2C=CF_2$ in the mixture to the compound(s) of formulas $C_dH_eF_fCl_gBr_hI_k$ and $Y^3Y^4C=CY^5Y^6$ in the mixture. In this invention, the term "selectively reacting", "selectively react" or "selective addition reaction" expresses the same concept that the selective removal agent more readily reacts with the component (1) compounds than the component (2) compounds. Preferably the mole ratio of selective removal agents to component (1) compounds is at least 1:1 and the selective removal agent reacts with at least 50 mole % of the component (1) compound, preferably at least 90 mole %, and most preferably at least 99 mole % of the component (1) compound. Typically no more than 30 mole % of the selective removal agent reacts with component (2) compound(s), and no more than 30 mole % of the component (2) compound(s) reacts with the selective removal agent.

Some component (2) compounds may isomerize or be transformed to other compounds. For example, the results in Example 11 suggest that Z-HFC-1234ze is isomerizes to E-HFC-1234ze in the presence of 1,1,2,2-tetrafluoroethanesulfonic acid and that HFC-245fa can be dehydrofluorinated to form HFC-1234ze in the presence of 1,1,2,2-tetrafluoroethanesulfonic acid.

Component (2) compounds can be saturated or unsaturated.

Examples of saturated compounds of component (2) include methane, ethane, propane, butane, pentane, 2-methylpropane, 2-methylbutane, 2,2-dimethylpropane, tetrafluoromethane (PFC-14), hexafluoroethane (PFC-116), octafluoropropane (PFC-218), decafluorobutane (PFC-31-10), fluoromethane (HFC-41), difluoromethane (HFC-32), trifluoromethane (HFC-23), fluoroethane (HFC-161), 1,1-difluoroethane (HFC-152a), 1,1,1-trifluoroethane (HFC-143a), 1,1,1,2-tetrafluoroethane (HFC-134a), 1,1,2,2-tetrafluoroethane (HFC-134), 1,1,1,2,2-pentafluoroethane (HFC-125), 1,1,1,3,3,3-hexafluoropropane (HFC-236fa), 1,1,1,2,3,3-hexafluoropropane (HFC-236ea), 1,1,2,2,3,3-hexafluoropropane (HFC-236ca), 1,1,1,2,2,3-hexafluoropropane (HFC-236cb), 1,1,1,2,2,3,3-heptafluoropropane (HFC-227ca), 1,1,1,2,3,3,3-heptafluoropropane (HFC-227ea), 1,1,1,3,3-pentafluoropropane (HFC-245fa), 1,1,1,2,2-pentafluoropropane (HFC-245cb), 1,1,2,2,3-pentafluoropropane (HFC-245ca), 1,1,1,2,3-pentafluoropropane (HFC-245ea), 1,1,1,2,3-pentafluoropropane (HFC-245eb), 1,1,1,2-tetrafluoropropane (HFC-254eb), 1,1,1,3-tetrafluoropropane (HFC-254fb), 1,2,2-trifluoropropane (HFC-263ca), 1,1,1-trifluoropropane (HFC-263fb), 2,2-difluoropropane (HFC-272ca), 1,1-difluoropropane (HFC-272fb), 1,1,1,2,4,4,4-hepafluorobutane (HFC-347mef), 1,1,2,2,3,3,4,4-octafluorobutane (HFC-338 pcc), 1,1,1,2,3,4,4,4-octafluorobutand (HFC-338mee), trichlorofluoromethane (CFC-11), dichlorodifluoromethane (CFC-12), 1,1,1-trichlorotrifluoroethane (CFC-113a), 1,1,2-trichlorotrifluoroethane (CFC-113), and chloropentafluoroethane (CFC-115), chlorodifluoromethane (HCFC-22), 2-chloro-1,1,1-trifluoroethane (HCFC-123), 2-chloro-1,1,1,2-tetrafluoroethane (HCFC-124), 1-chloro-1,1-difluoroethane (HCFC-142b), 2,2-dichloro-1,1,1,3,3,3-hexafluoropropane (CFC-216aa), 1,2-dichloro-1,1,2,3,3,3-hexafluoropropane (CFC-216ba), 1,1-dichloro-1,2,2,3,3,3-hexafluoropropane (CFC-216cb), 1,3-dichloro-1,1,2,2,3,3-hexafluoropropane (CFC-216ca), 1,2,2-trichloro-1,1,3,3,3-pentafluoropropane (CFC-215aa), 1,2,3-trichloro-1,1,2,3,3-pentafluoropropane (CFC-215ba), 1,1,2-trichloro-1,2,3,3,3-pentafluoropropane (CFC-215bb), 1,1,1-trichloro-2,2,3,3,3-pentafluoropropane (CFC-215cb), 1,1,3-trichloro-1,2,2,3,3-pentafluoropropane (CFC-215ca), 2-chloro-1,1,1,2,3,3,3-heptafluoropropane (CFC-217ba), 1-chloro-1,1,2,2,3,3,3-heptafluoropropane (CFC-217ca), 2-chloro-1,1,1,2,3,3-hexafluoropropane (HCFC-226ba), 2-chloro-1,1,1,3,3,3-hexafluoropropane (HCFC-226da), and 1,2-dichloro-1,2,3,3,3-pentafluoropropane (HCFC-225ba), Of particular note are saturated component (2) compounds selected from the group consisting of difluoromethane (HFC-32), trifluoromethane (HFC-23), fluoroethane (HFC-161), 1,1-difluoroethane (HFC-152a), 1,1,1-trifluoroethane (HFC-143a), 1,1,1,2-tetrafluoroethane (HFC-134a), 1,1,2,2-tetrafluoroethane (HFC-134), 1,1,1,2,2-pentafluoroethane (HFC-125), 1,1,1,3,3,3-hexafluoropropane (HFC-236fa), 1,1,1,2,3,3-hexafluoropropane (HFC-236ea), 1,1,2,2,3,3-hexafluoropropane (HFC-236ca), 1,1,1,2,2,3-hexafluoropropane (HFC-236cb), 1,1,1,2,2,3,3-heptafluoropropane (HFC-227ca), 1,1,1,2,3,3,3-heptafluoropropane (HFC-227ea), 1,1,1,3,3,3-pentafluoropropane (HFC-245fa), 1,1,1,2,2-pentafluoropropane (HFC-245cb), 1,1,2,2,3-pentafluoropropane (HFC-245ca), 1,1,2,3,3-pentafluoropropane (HFC-245ea), 1,1,1,2,3-pentafluoropropane (HFC-245eb), 1,1,1,2-tetrafluoropropane (HFC-254eb), 1,1,1,3-tetrafluoropropane (HFC-254fb), and 1,1,1-trifluoropropane (HFC-263fb).

Examples of unsaturated component (2) compounds include 1,3,3,3-tetrafluoro-1-propene (HFC-1234ze), 2,3,3,3-tetrafluoro-1-propene (HFC-1234yf), 1,2,3,3,3-pentafluoro-1-propene (HFC-1225ye), 1,1,1,4,4,4-hexafluoro-2-butene (HFC-1338m/z), 1,1,1,3,4,4,5,5,5-nonafluoro-2-pentene (HFC-1429mzy), 1,1,1,2,4,4,5,5,5-nonafluoro-2-pentene (HFC-1429myz), 1,1,1,3,3,4,4,4-octafluoro-2-pentene (HFC-1438m/z), 2-chloro-3,3,3-trifluoro-1-propene, 1,2,2-trichloro-3,3,3-trifluoro-1-propene, 1,2-dichloro-3,3,3-trifluoro-1-propene, 1,2,3,3,3-tetrafluoro-1-propene, 2,3,3-trifluoro-1-propene, 3,3,3-trifluoro-1-propene, 1,2,3-trifluoro-1-propene, 1,3,3-trifluoro-1-propene, 2-chloro-1,1,1,4,4,4-hexafluoro-2-butene, 2,3-dichloro-1,1,1,4,4,4-hexafluoro-2-butene, 1,1,1,2,3,4,4,4-octafluoro-2-butene, 1,1,1,2,4,4,4-heptafluoro-2-butene, 1,2,3,3,4,4,4-heptafluoro-1-butene, 1,1,1,2,3,4,4-heptafluoro-2-butene, 1,3,3,3-tetrafluoro-2-(trifluoromethyl)-2-propene, 2,3,3,4,4,4-hexafluoro-1-butene, 1,3,3,4,4,4-hexafluoro-1-butene, 1,2,3,4,4,4-hexafluoro-1-butene, 1,2,3,3,4,4-hexafluoro-1-butene 1,1,2,3,4,4-hexafluoro-2-butene, 1,1,1,2,3,4-hexafluoro-2-butene, 1,1,1,2,3,3-hexafluoro-2-butene, 1,1,1,3,4,4-hexafluoro-2-butene, 3,3,3-trifluoro-2-(trifluoromethyl)-1-propene, 1,1,1,2,4-pentafluoro-2-butene, 1,1,1,3,4-pentafluoro-2-butene, 3,3,4,4,4-pentafluoro-1-butene, 1,1,1,4,4-pentafluoro-2-butene, 1,1,1,2,3-pentafluoro-2-butene, 2,3,3,4,4-pentafluoro-1-butene, 1,1,2,4,4-pentafluoro-2-butene, 1,1,2,3,4-pentafluoro-2-butene, 1,2,3,3,4-pentafluoro-1-butene, 2-(difluoromethyl)-3,3,3-trifluoro-1-propene, 3,3,4,4-tetrafluoro-1-butene, 1,3,3,3-tetrafluoro-2-methyl-1-propene, 2-(difluoromethyl)-3,3-difluoro-1-propene, 1,1,1,2-tetrafluoro-2-butene, 1,1,1,3-tetrafluoro-2-butene, 1,1,1,2,3,4,4,5,5,5-decafluoro-2-pentene, 1,1,1,4,4,4-hexafluoro-2-(trifluoromethyl)-2-butene, 1,2,3,3,4,4,5,5,5-nonafluoro-1-pentene, 1,1,2,3,4,4,5,5,5-nonafluoro-2-pentene, 1,1,1,2,3,4,4,5,5-nonafluoro-2-pentene, 1,1,1,2,3,4,5,5,5-nonafluoro-2-pentene, 1,2,3,4,4,4-hexafluoro-3-(trifluoromethyl)-1-butene, 1,1,1,4,4,4-hexafluoro-3-(trifluoromethyl)-2-butene, 2,3,3,4,4,5,5-octafluoro-1-pentene, 1,2,3,3,4,4,5,5-octafluoro-1-pentene, 3,3,4,4-pentafluoro-2-(trifluoromethyl)-1-butene, 1,3,4,4,4-pentafluoro-3-(trifluoromethyl)-1-butene, 1,1,4,4,5,5,5-octafluoro-2-pentene, 3,4,4,4-tetrafluoro-3-(trifluoromethyl)-1-butene, 3,3,4,4,5,5,5-heptafluoro-1-pentene, 2,3,3,4,4,5,5-heptafluoro-1-pentene, 1,1,1,2,4,4,4-heptafluoro-3-methyl-2-butene, 2,4,4,4-tetrafluoro-3-(trifluoromethyl)-1-butene, 1,4,4,4-tetrafluoro-3-(trifluoromethyl)-1-butene, 1,4,4,4-tetrafluoro-3-(trifluoromethyl)-2-butene, 2,4,4,4-tetrafluoro-3-(trifluoromethyl)-2-butene, 3-(trifluoromethyl)-4,4,4-trifluoro-2-butene, 3,4,4,5,5,5-hexafluoro-2-pentene, 1,1,1,4,4,4-hexafluoro-2-methyl-2-butene, 3,3,4,5,5,5-hexafluoro-1-pentene, 4,4,4-trifluoro-2-(trifluoromethyl)-1-butene, 1,1,1,2,2,3,4,5,5,6,6,6-dodecafluoro-3-hexene, 1,1,1,4,4,4-hexafluoro-2,3-bis(trifluoromethyl)-2-butene, 1,1,1,4,4,5,5,5-octafluoro-2-trifluoromethyl-2-pentene, 1,1,1,3,4,5,5,5-octafluoro-4-(trifluoromethyl)-2-pentene, 1,1,1,4,5,5,5-heptafluoro-4-(trifluoromethyl)-2-pentene, 1,1,1,4,4,5,5,6,6,6-decafluoro-2-hexene, 1,1,1,2,2,5,5,6,6,6-decafluoro-3-hexene, 3,3,4,4,5,5,6,6,6-nonafluoro-1-hexene, 4,4,4-trifluoro-3,3-bis(trifluoromethyl)-1-butene, 1,1,1,4,4,4-hexafluoro-3-methyl-2-(trifluoromethyl)-2-butene, 2,3,3,5,5,5-hexafluoro-4-(trifluoromethyl)-1-pentene, 1,1,1,2,4,4,5,5,5-nonafluoro-3-methyl-2-pentene, 1,1,1,5,5,5-hexafluoro-4-(trifluoromethyl)-2-pentene, 3,4,4,5,5,6,6,6-octafluoro-2-hexene, 3,3,4,4,5,5,6,6-octafluoro-2-hexene, 1,1,1,4,4-pentafluoro-2-(trifluoromethyl)-2-pentene, 4,4,5,5,5-pentafluoro-2-(trifluoromethyl)-1-pentene, 3,3,4,4,5,5-heptafluoro-2-methyl-1-pentene, 1,1,1,2,3,4,4,5,5,6,6,7,7,7-tetradecafluoro-2-heptene, 1,1,1,2,2,3,4,5,5,6,6,7,7,7-tetradecafluoro-2-heptene, 1,1,1,3,4,4,5,5,6,6,7,7,7-tridecafluoro-2-heptene, 1,1,1,2,4,4,5,5,6,6,7,7,7-tridecafluoro-2-heptene, 1,1,1,2,2,4,5,5,6,6,7,7,7-tridecafluoro-3-heptene, 1,1,1,2,2,3,5,5,6,6,7,7,7-tridecafluoro-3-heptene, 4,4,5,5,6,6,6-heptafluoro-2-hexene, 4,4,5,5,6,6,6-heptafluoro-1-hexene, 1,1,1,2,2,3,4-heptafluoro-3-hexene, 4,5,5,5-tetrafluoro-4-(trifluoromethyl)-1-pentene, 1,1,1,2,5,5,5-heptafluoro-4-methyl-2-pentene, 1,1,1,3-tetrafluoro-2-(trifluoromethyl)-2-pentene, 1,1,1,2,3,4,5,5-nonafluoro-4-(trifluoromethyl)-2-pentene. Of particular note are unsaturated component (2) compounds selected from the group consisting of 1,3,3,3-tetrafluoro-1-propene (HFC-1234ze), 2,3,3,3-tetrafluoro-1-propene (HFC-1234yf), 1,2,3,3,3-pentafluoro-1-propene (HFC-1225ye), 1,1,1,4,4,4-hexafluoro-2-butene (HFC-1338m/z), 1,1,1,3,4,4,5,5,5-nonafluoro-2-pentene (HFC-1429mzy), 1,1,1,2,4,4,5,5,5-nonafluoro-2-pentene (HFC-1429myz), 1,1,1,3,3,4,4,4-octafluoro-2-pentene (HFC-1438m/z), 2-chloro-3,3,3-trifluoro-1-propene, 1,2,2-trichloro-3,3,3-trifluoro-1-propene, 1,2-dichloro-3,3,3-trifluoro-1-propene, 1,2,3,3-tetrafluoro-1-propene, and 3,3,3-trifluoro-1-propene.

One embodiment of this invention is processes wherein the mole ratio of HFC-1225zc to HFC-1225ye in a mixture comprising HFC-1225zc and HFC-1225ye is reduced.

Another embodiment of this invention is processes wherein the mole ratio of HFC-1123 to HFC-1225ye in a mixture comprising HFC-1123 and HFC-1225ye is reduced.

Another embodiment of this invention is processes wherein the mole ratio of HFC-1225zc to the total of HFC-1429mzy and HFC-1429myz in a mixture comprising HFC-1225zc, HFC-1429mzy and HFC-1429myz is reduced.

Another embodiment of this invention is processes wherein the mole ratio of HFC-1225zc to the total of HFC-1225ye and HFC-236ea in a mixture comprising HFC-1225zc, HFC-1225ye and HFC-236ea is reduced.

Another embodiment of this invention is processes wherein the mole ratio of HFC-1123 to the total of HFC-1225ye and HFC-236ea in a mixture comprising HFC-1123, HFC-1225ye and HFC-236ea is reduced.

Another embodiment of this invention is processes wherein the mole ratio of HFC-1225zc to the total of HFC- 1429mzy, HFC-1429myz, and HFC-43-10mee in a mixture comprising HFC-1225zc, HFC-1429mzy, HFC-1429myz and HFC-43-10mee is reduced.

The contacting step of this invention can be accomplished in several ways. In one embodiment of this invention, the mixture comprising component (1) and component (2) compounds is a vapor and the selective removal agent is a liquid. The vapor is bubbled through the liquid with agitation.

In another embodiment of this invention, both the mixture comprising component (1) and component (2) compounds and the selective removal agent are liquids, and they are simply mixed together under the autogenous pressure of the reactants.

In another embodiment of this invention, the selective removal agent is attached as an end group on polymer main chains, such as Nafion®, or supported on a carrier such as carbon, graphite, silica, alumina, boron nitride, or silicon carbide. The mixture comprising component (1) and component (2) compounds can be either vapor or liquid which flows over the selective removal agent.

Selective removal of component (1) compounds may be carried out over a wide temperature range. Typically reaction temperatures are from about −10° C. to about 150° C. Preferably the reaction is carried out from about 20° C. to about 50° C.

The mole ratio of the selective removal agent to component (1) compound(s) in the mixture is typically from about 1:1 to about 10:1.

Selective reaction of the selective removal agent with the component (1) compounds can be facilitated by adjusting the temperature, mole ratio of the selective removal agent to the component (1) compounds, and in the case of oleum the concentration of $SO_3$ therein. The effectiveness of sulfuric acid as a selective removal agent may be enhanced by removal of water or addition of $SO_3$.

Of note are embodiments of this invention where at least one product compound selected from compounds of the formula $C_dH_eF_fCl_gBr_hI_k$ and compounds of the formula $Y^3Y^4C=CY^5Y^6$ is recovered from a mixture comprising (i) said at least one product compound and (ii) at least one olefinic impurity of the formula $Y^1Y^2C=CF_2$. Recovery is accomplished by contacting the mixture with a selective removal agent as described above; and separating the at least one product compound from the reaction product of the olefinic impurity with the selective removal agent. Separation can be accomplished by conventional means such as distillation or phase separation.

Of note are embodiments wherein prior to contact the olefinic impurity is present in the mixture in one mole percent or less (for example, 100-10,000 ppm).

In one embodiment of this invention, the product compound can be recovered by separating it from the reaction product by distillation. For example, selective addition reaction between fluorosulfonic acid ($HOSO_2F$) and a mixture containing HFC-1225ye and HFC-1225zc results in a mixture containing unreacted HFC-1225ye and 1,1,3,3,3-pentafluoropropyl fluorosulfate ($CF_3CH_2CF_2OSO_2F$). HFC-1225ye has boiling point of −19.9° C., and 1,1,3,3,3-pentafluoropropyl fluorosulfate has boiling point of 94-96° C. The product compound HFC-1225ye can be easily recovered by distillation.

In another embodiment of this invention, the product compound can be recovered by separating it from the reaction product by scrubbing with water or weak alkaline solution. For example, treatment of a mixture containing HFC-1225ye and HFC-1225zc results in 1,1,3,3,3-pentafluoropropane-β-sultone together with unreacted HFC-1225ye. The sultone could be hydrolyzed to form 2,2,2-trifluoroethanesulfonic acid which is soluble in water or weak alkaline aqueous solution. Thus, 2,2,2-trifluoroethanesulfonic acid could be scrubbed away from the mixture, leaving pure HFC-1225ye.

EXAMPLES

Example 1

10 ml of fluorosulfonic acid ($HOSO_2F$) was put into a 25 ml three necked flask equipped with a dry ice condenser, magnetic stirrer, thermometer and exit bubbler. Then 7.5 g of 1,1,3,3,3-pentafluoropropene was bubbled through the fluorosulfonic acid during 30 minutes with vigorous agitation. The temperature of reaction mixture increased from 21° C. to 40° C. According to $^{19}F$ and $^1H$ NMR, the product mixture contained only $CF_3CH_2CF_2OSO_2F$ and fluorosulfonic acid and no detectable amount of HFC-1225zc. Distillation gave 11 g (83%) of 1,1,3,3,3-pentafluoropropyl fluorosulfate, b.p. 94-96° C.

Example 2

Comparative

Other conditions were the same as in Example 1. After bubbling of 7.5 g of HFC-1225ye (1,2,3,3,3-pentafluoropropene) through 10 ml of fluorosulfonic acid at 20-30° C., the $^{19}F$ NMR showed that the reaction mixture only contained about 7 mol % of HFC-1225ye in $HOSO_2F$.

Example 3

A 100 ml shaker tube was charged with 10 g of $SO_3$ (without stabilizer) and then cooled in liquid nitrogen and evacuated. A 60 g mixture of pentafluoropropenes (93 wt % HFC-1225ye and 7 wt % HFC-1225zc) was added, and the tube was heated up to 20° C. and was shaken for 2 hours. When the tube was evacuated, 54 g of HFC-1225ye (as determined by GC and NMR) was collected in the cold trap. Distillation of the liquid in the shaker tube gave 5.1 g of 1,1,3,3,3-pentafluoropropane-β-sultone, b.p. 89-92° C.

Example 4

A 150 mL stainless steel cylinder was charged with 7 grams of fluorosulfuric acid and 14 grams of a mixture containing E- and Z-1,2,3,3,3-pentafluoro-1-propene (HFC-1225ye), 1,1,1,2,3,3-hexafluoropropane (HFC-236ea), and trifluoroethene (HFC-1123). The cylinder was allowed to stand at room temperature for about 21 hours with occasional shaking. The GC analysis of the mixture before and after contacting with fluorosulfuric acid is given in the Table below.

| | GC Area % | |
|---|---|---|
| Component | Initial | Final |
| Z-HFC-1225ye | 96.4 | 99.1 |
| E-HFC-1225ye | 0.5 | 0.6 |
| HFC-236ea | 0.3 | 0.3 |
| HFC-1123 | 2.6 | 0.024 |

Example 5

Example 4 was repeated except that 8 grams of 30% oleum (30% $SO_3$ in $H_2SO_4$) and 26 g of the fluorocarbon mixture were added to the cylinder. After about 16 hours at room temperature, the contents of the cylinder were vented through an aqueous potassium hydrogen phosphate buffer and dried over soda lime and calcium sulfate. GC analysis of the recovered product (21 grams) is given in the Table below.

| Component | GC Area %<br>Recovered Product |
|---|---|
| Z-HFC-1225ye | 99.0 |
| E-HFC-1225ye | 0.6 |
| HFC-236ea | 0.4 |
| HFC-1123 | 0.009 |

Example 6

A 150 mL stainless steel cylinder was charged with 17 grams of 96% sulfuric acid and 36 grams of a mixture containing E- and Z-1,2,3,3,3-pentafluoro-1-propene (HFC-1225ye), 1,1,1,2,3,3-hexafluoropropane (HFC-236ea), and trifluoroethene (HFC-1123). The cylinder was allowed to stand at room temperature for 17.5 hours with occasional shaking. The GC analysis of the mixture before and after contacting with sulfuric acid is given in the Table below.

| Component | GC Area % | |
|---|---|---|
| | Initial | Final |
| Z-HFC-1225ye | 95.1 | 96.5 |
| E-HFC-1225ye | 0.56 | 0.53 |
| HFC-236ea | 0.27 | 0.49 |
| HFC-1123 | 3.97 | 2.45 |
| Unidentified | 0.051 | 0.038 |

Example 7

Trifluoromethane sulfonic acid (7 grams) and 35 g of the fluorocarbon mixture used in Comparative Example 6 were added to a 150 mL stainless steel cylinder. After about 16 hours at room temperature, the contents of the cylinder were vented through an aqueous potassium hydrogen phosphate buffer and dried over soda lime and calcium sulfate. GC analysis of the recovered product (30 grams) is given in the Table below.

| Component | GC Area %<br>Recovered Product |
|---|---|
| Z-HFC-1225ye | 99.2 |
| E-HFC-1225ye | 0.46 |
| HFC-236ea | 0.23 |
| HFC-1123 | 0.083 |
| Unidentified | 0.027 |

Example 8

A 400 mL shaker tube was charged with 33 grams of 30% oleum. The tube was sealed, cooled in dry ice, evacuated, and charged with 100 grams of a mixture containing E- and Z-1,2,3,3,3-pentafluoro-1-propene (HFC-1225ye), 1,1,1,2,3,3-hexafluoropropane (HFC-236ea), and trifluoroethene (HFC-1123). The tube was shaken for 12 hours at 31-39° C. The volatile contents of the tube were recovered by vacuum transfer, scrubbed using an aqueous potassium hydrogen phosphate buffer, and dried over soda lime and calcium sulfate to give 84 grams of product. The GC analysis of the fluorocarbon mixture before and after contacting with oleum is given in the Table below.

| Component | GC Area % | |
|---|---|---|
| | Initial | Final |
| Z-HFC-1225ye | 98.0 | 96.9 |
| E-HFC-1225ye | 0.69 | 0.73 |
| HFC-236ea | 1.33 | 2.40 |
| HFC-1123 | 0.011 | 0.001 |

Example 9

A 1 L rocker tube was charged with 135.8 grams of 30% oleum. The tube was sealed, cooled in dry ice, evacuated, and charged with 444 grams of the fluorocarbon mixture used in Example 7. The tube was rocked for 21 hours at 30-31° C. The volatile contents of the tube were scrubbed using an aqueous potassium hydrogen phosphate buffer and dried over soda lime and calcium sulfate. The GC analysis of the scrubbed product (404 grams) is given in the Table below.

| Component | GC Area %<br>Scrubbed product |
|---|---|
| Z-HFC-1225ye | 99.0 |
| E-HFC-1225ye | 0.56 |
| HFC-236ea | 0.45 |
| HFC-1123 | 0.002 |

Example 10

A 150 mL stainless steel cylinder was charged with 12.2 grams of 30% oleum and 29.9 grams of a mixture containing 1,1,1,2,4,4,5,5,5-nonafluoro-2-pentene (HFC-1429myz), 1,1,1,3,4,4,5,5,5-nonafluoro-2-pentene (HFC-1429mzy), 1,1,1,2,3,4,4,5,5,5-decafluoropentane (HFC-43-10mee), and about 5 weight percent 1,1,3,3,3-pentafluoro-1-propene (HFC-1225zc). The cylinder was allowed to stand at room temperature for about 163 hours with occasional shaking. The GC analysis of the vapor phase of the mixture after contacting with oleum indicated that HFC-1225zc was present at a concentration of 0.35 GC area % compared with 9.6 GC area % prior to contacting with oleum.

Example 11

A 150 mL stainless steel cylinder was charged with 10.1 grams of 1,1,2,2-tetrafluoroethanesulfonic acid and 33.2 grams of a mixture containing E- and Z-1,3,3,3-tetrafluoro-1-propene (HFC-1234ze), 1,1,1,3,3-pentafluoropropane (HFC-245fa), and about 5.6 weight percent 1,1,3,3,3-pentafluoro-1-propene (HFC-1225zc). The cylinder was allowed to stand at room temperature for about 162 hours with occasional shaking. The GC analysis of the vapor phase of the mixture before and after contacting with 1,1,2,2-tetrafluoro-ethanesulfonic acid is shown in the Table below.

|  | GC Area % | |
| --- | --- | --- |
| Component | Initial | Final |
| E-HFC-1234ze | 10.5 | 42.3 |
| Z-HFC-1234ze | 20.2 | 11.0 |
| HFC-245fa | 52.2 | 46.6 |
| HFC-1225zc | 17.1 | 0.049 |

Example 12

Following a procedure similar to that in Example 9, 429 grams of a mixture containing E- and Z-1,2,3,3,3-pentafluoro-1-propene and trifluoroethene were contacted with 126.9 grams of 30% oleum for 67 hours at 30° C. GC analysis of the starting material and scrubbed, recovered product (415 grams) is given in the Table below.

|  | GC Area % | |
| --- | --- | --- |
| Component | Initial | Final |
| Z-HFC-1225ye | 99.53 | 99.57 |
| E-HFC-1225ye | 0.44 | 0.42 |
| HFC-1123 | 0.027 | <0.001 |

Example 13

A 250 mL Hastelloy shaker tube was loaded with 60 g (0.51 mole) chlorosulfuric acid ($HOSO_2Cl$), cooled in liquid nitrogen, evacuated and loaded with 60 g (0.45 mole) of 1,1,3,3,3-pentafluoropropene. The reaction vessel was allowed to warm and kept on a shaker at 20° C. at autogenous pressure for 24 hours. After 24 hours, the pressure tube was unloaded, and the reaction mixture quenched by ice and the organic layer washed with 5% sodium bicarbonate, water and dried under $MgSO_4$. After distillation, 81.3 g of $CF_3CH_2CF_2OSO_2Cl$ was obtained containing 6% of $CF_3CH_2CF_2OSO_2F$.

Example 14

In the three neck flask equipped with a condenser, thermometer, magnetic stirrer and bubbling tube was loaded 50 g (0.43 mole) of $HOSO_2Cl$. 1,1,3,3,3-Pentafluoropropene (25 g, 0.19 mole) was bubbled through the solution at 40° C. for 30 minutes. Then the reaction mixture was poured onto ice, the organic layer was separated, washed with a solution of sodium bicarbonate, and dried with $MgSO_4$. After distillation 35 g of $CF_3CH_2CF_2OSO_2Cl$ was obtained containing 4% of $CF_3CH_2CF_2OSO_2F$.

Example 15

A 100 mL Hastelloy shaker tube was loaded with 26.5 g (0.227 mole) chlorosulfuric acid, cooled in liquid nitrogen, evacuated and loaded with 30 g (0.225 mole) of 1,1,3,3,3-pentafluoropropene. The reaction vessel was allowed to warm and kept on a shaker at 40° C. at autogenous pressure for 6 hours. The pressure tube was unloaded, and the reaction mixture was added drop by drop into the flask containing 60 ml of ethanol at −10° C. over a 15 minute period. The reaction mixture was stirred overnight at 20° C. and then was poured into 200 ml of ice water. The organic layer was separated, washed with sodium bicarbonate, water, and dried under $MgSO_4$. Distillation gave 31 g of $CF_3CH_2COOEt$ (87%), bp 108-109° C.

Example 16

Analogous to Example 15, a reaction product prepared from 30 g of 1,1,3,3,3-pentafluoropropene and 26.5 g of chlorosulfuric acid was reacted with 50 ml of methanol at −10° C. After treatment and distillation 23 g of $CF_3CH_2COOMe$ (72%) bp 98° C. was obtained.

Example 17

Comparative

A 150 mL stainless steel cylinder was charged with 10.6 grams of 24% oleum and 25.4 grams of a mixture containing 57.3 mole percent 2,3,3,3-tetrafluoro-1-propene (HFC-1234yf), 19.2 mole percent 1,1,1,2,2-pentafluoropropane (HFC-245cb), and 23.5 mole percent 3,3,3-trifluoropropene (HFC-1243zf). The cylinder was allowed to stand at room temperature for about 63.7 hours with occasional shaking. The GC and NMR analysis of the mixture before and after contact with oleum indicated that essentially no reaction had occurred.

Example 18

Comparative

A 150 mL stainless steel cylinder was charged with 10.7 grams of 30% oleum and 50.8 grams of a mixture containing 2-chloroheptafluoropropane (CFC-217ba), 1,1,1,2,3,3,3-heptafluoropropane (HFC-227ea), and hexafluoropropene (HFP). The cylinder was allowed to stand at room temperature for about 119 hours with occasional shaking. The GC analysis of the vapor phase of the mixture before and after contacting with oleum showed little change in the concentration of HFP in the sample.

Example 19

A 70 mL stainless steel tube was charged with 15 grams of 30% oleum and 36.4 grams of a mixture containing 2-chloroheptafluoropropane (CFC-217ba), 1,1,1,2,3,3,3-heptafluoropropane (HFC-227ea), 1,1,1,2,3,3-hexafluoropropane (HFC-236ea), and hexafluoropropene (HFP). The tube was shaken for about 12 hours at 60° C. The volatile components from the tube were passed through a solution of potassium hydrogen phosphate, dried over soda lime/calcium sulfate and collected in a trap chilled in dry ice (23.1 g). The GC analysis of the vapor phase of the mixture before and after contacting with oleum showed a slight decrease in the concentration of HFP in the sample.

|  | GC Area % | |
| --- | --- | --- |
| Component | Initial | Final |
| HFP | 17.0 | 10.8 |
| HFC-227ea | 2.3 | 2.1 |

-continued

| | GC Area % | |
|---|---|---|
| Component | Initial | Final |
| CFC-217ba | 79.9 | 86.5 |
| HFC-236ea | 0.5 | 0.4 |

Example 20

A 150 mL stainless steel tube was charged with 12.9 grams of 67% oleum and 36.5 grams of a mixture containing 2-chloroheptafluoropropane (CFC-217ba), 1,1,1,2,3,3,3-heptafluoropropane (HFC-227ea), 1,1,1,2,3,3-hexafluoropropane (HFC-236ea), and hexafluoropropene (HFP). The cylinder was allowed to stand at room temperature for about 66.7 hours with occasional shaking. The volatile components from the tube were passed through a solution of potassium hydrogen phosphate, dried over soda lime/calcium sulfate and collected in a trap chilled in dry ice (28.3 g). The NMR analysis of the vapor phase of the mixture before and after contacting with oleum showed a significant decrease in the concentration of HFP in the sample.

| | Mole % | |
|---|---|---|
| Component | Initial | Final |
| HFP | 13.8 | 3.3 |
| HFC-227ea | 2.2 | 3.3 |
| CFC-217ba | 83.3 | 91.8 |
| HFC-236ea | 0.7 | 1.7 |

What is claimed is:

1. A process for reducing the mole ratio of a (1) first component selected from the group consisting of compounds of the formula $Y^1Y^2C=CF_2$ wherein $Y^1$ and $Y^2$ are each independently H, F, Cl, Br, $C_1$-$C_6$ alkyl or $C_1$-$C_6$ haloalkyl containing no more than 3 chlorine substituents, 2 bromine substituents and 1 iodo substituent to a (2) second component selected from the group consisting of saturated compounds of the formula $C_dH_eF_fCl_gBr_hI_k$ wherein d is an integer from 1 to 10, and e+f+g+h+k is equal to 2d+2, provided that g is 0, 1, 2 or 3, h is 0, 1 or 2 and k is 0 or 1 and unsaturated compounds of the formula $Y^3Y^4C=CY^5Y^6$, wherein $Y^3$, $Y^5$ and $Y^6$ are each independently H, F, Cl, Br, $C_1$-$C_6$ alkyl or $C_1$-$C_6$ haloalkyl containing no more than 3 chlorine substituents, 2 bromine substituents and 1 iodo substituent, provided that $Y^5$ and $Y^6$ are not both F, and $Y^4$ is $C_1$-$C_6$ alkyl or $C_1$-$C_6$ haloalkyl containing no more than 3 chlorine substituents, 2 bromine substituents and 1 iodo substituent, in a mixture comprising said first component and second component, comprising:

contacting said mixture with at least one selective removal agent selected from the group consisting of $SO_3$ and $RSO_3H$, wherein R is selected from the group consisting of F, Cl, OH, $C_1$-$C_8$ alkyl, $C_1$-$C_8$ fluoroalkyl, and $C_1$-$C_8$ fluoroalkoxyalkyl containing no more than two ether oxygens to selectively react said selective removal agent with said first component.

2. The process of claim 1 wherein the component (1) compounds are selected from the group consisting of 1,1,3,3,3-pentafluoropropene (HFC-1225zc), trifluoroethylene (HFC-1123), tetrafluoroethylene (TFE), chlorotrifluoroethylene (CTFE), 1-chloro-2,2-difluoroethene, 2-chloro-1,1,3,3,3-pentafluoro-1-propene (CFC-1215xc), 2-bromo-1,1,3,3,3-pentafluoro-1-propene (CFC-1215xcB), hexafluoropropene (HFP), and perfluoroisobutylene (PFIB), 1,1,2,3,3-pentafluoro-1-propene, 1,1,2,3-tetrafluoro-1-propene, 1,1,3,3-tetrafluoro-1-propene, 1,1,2-trifluoro-1-propene, and 1,1,3-trifluoro-1-propene.

3. The process of claim 1 wherein the saturated component (2) compounds are selected from the group consisting of difluoromethane (HFC-32), trifluoromethane (HFC-23), fluoroethane (HFC-161), 1,1-difluoroethane (HFC-152a), 1,1,1-trifluoroethane (HFC-143a), 1,1,1,2-tetrafluoroethane (HFC-134a), 1,1,2,2-tetrafluoroethane (HFC-134), 1,1,1,2,2-pentafluoroethane (HFC-125), 1,1,1,3,3,3-hexafluoropropane (HFC-236fa), 1,1,1,2,3,3-hexafluoropropane (HFC-236ea), 1,1,2,2,3,3-hexafluoropropane (HFC-236ca), 1,1,1,2,2,3-hexafluoropropane (HFC-236cb), 1,1,1,2,2,3,3-heptafluoropropane (HFC-227ca), 1,1,1,2,3,3,3-heptafluoropropane (HFC-227ea), 1,1,1,3,3-pentafluoropropane (HFC-245fa), 1,1,1,2,2-pentafluoropropane (HFC-245cb), 1,1,2,2,3-pentafluoropropane (HFC-245ca), 1,1,2,3,3-pentafluoropropane (HFC-245ea), 1,1,1,2,3-pentafluoropropane (HFC-245eb), 1,1,1,2-tetrafluoropropane (HFC-254eb), 1,1,1,3-tetrafluoropropane (HFC-254fb), and 1,1,1-trifluoropropane (HFC-263fb).

4. The process of claim 1 wherein the unsaturated component (2) compounds are selected from the group consisting of 1,3,3,3-tetrafluoro-1-propene (HFC-1234ze), 2,3,3,3-tetrafluoro-1-propene (HFC-1234yf), 1,2,3,3,3-pentafluoro-1-propene (HFC-1225ye), 1,1,1,4,4,4-hexafluoro-2-butene (HFC-1338m/z), 1,1,1,3,4,4,5,5,5-nonafluoro-2-pentene (HFC-1429mzy), 1,1,1,2,4,4,5,5,5-nonafluoro-2-pentene (HFC-1429myz), 1,1,1,3,3,4,4,4-octafluoro-2-pentene (HFC-1438m/z), 2-chloro-3,3,3-trifluoro-1-propene, 1,2,2-trichloro-3,3,3-trifluoro-1-propene, 1,2-dichloro-3,3,3-trifluoro-1-propene, 1,2,3,3-tetrafluoro-1-propene, and 3,3,3-trifluoro-1-propene.

5. The process of claim 1 wherein said selective removal agent is selected from the group consisting of $SO_3$, oleum, fluorosulfonic acid, chlorosulfonic acid, trifluoromethanesulfonic acid, 1,1,2,2-tetrafluoroethanesulfonic acid, 1,1,1,2-tetrafluoroethanesulfonic acid, 1,1,1,2,3,3-hexafluoropropane sulfonic acid, and methane sulfonic acid.

6. The process of claim 1 wherein said reaction is carried out at a temperature from about 20° C. to about 50° C.

7. The process of claim 1 wherein the component (2) compounds are unsaturated compounds.

8. The process of claim 7 wherein the reaction of the selective removal agent and the component (1) compound forms a fluorine-containing β-sultone or a sulfate.

9. The process of claim 8 wherein component (1) is trifluoroethylene, 1,1,3,3,3-pentafluoropropene or a mixture thereof, component (2) is 1,2,3,3,3-pentafluoro-1-propene, and said selective removal agent is selected from the group consisting of $SO_3$, oleum, fluorosulfonic acid, chlorosulfonic acid, trifluoromethanesulfonic acid, 1,1,2,2-tetrafluoroethanesulfonic acid, 1,1,1,2-tetrafluoroethanesulfonic acid, and 1,1,1,2,3,3-hexafluoropropane sulfonic acid.

10. A process for recovering at least one product compound selected from the group consisting of saturated compounds of the formula $C_dH_eF_fCl_gBr_hI_k$ wherein d is an integer from 1 to 10, and e+f+g+h+k is equal to 2d+2, provided that g is 0, 1, 2 or 3, h is 0, 1 or 2 and k is 0 or 1 and unsaturated compounds of the formula $Y^3Y^4C=CY^5Y^6$, wherein $Y^3$, $Y^5$ and $Y^6$ are each independently H, F, Cl, Br, $C_1$-$C_6$ alkyl or $C_1$-$C_6$ haloalkyl containing no more than 3 chlorine substituents, 2 bromine substituents and 1 iodo substituent, provided that $Y^5$ and $Y^6$ are not both F, and $Y^4$ is $C_1$-$C_6$ alkyl or $C_1$-$C_6$ haloalkyl containing no more than 3 chlorine substituents, 2 bromine substituents and 1 iodo substituent from a mixture comprising (i) said at least one product compound and (ii) olefinic impurity selected from the group consisting of compounds of the formula $Y^1Y^2C\!=\!CF_2$ wherein $Y^1$ and $Y^2$ are each independently H, F, Cl, Br, $C_1$-$C_6$ alkyl or $C_1$-$C_6$ haloalkyl containing no more than 3 chlorine substituents, 2 bromine substituents and 1 iodo substituent, comprising:

(a) contacting said mixture with at least one selective removal agent selected from the group consisting of $SO_3$ and $RSO_3H$, wherein R is selected from the group consisting of F, Cl, OH, $C_1$-$C_8$ alkyl, $C_1$-$C_8$ fluoroalkyl, and $C_1$-$C_8$ fluoroalkoxyalkyl containing no more than two ether oxygens to selectively react said selective removal agent with said olefinic impurity, thereby reducing the ratio of olefinic impurity to said at least one product compound; and (b) separating said at least one product from the reaction product of the olefinic impurity with the selective removal agent produced in (a).

* * * * *